United States Patent [19]

Suzuki et al.

[11] 4,430,746
[45] Feb. 7, 1984

[54] TOMOGRAPH FOR PHOTOGRAPHING ENTIRE JAWS

[75] Inventors: Masakazu Suzuki, Shin Nakamachi; Toshiaki Ikeda, Yahata; Shuhei Furuichi, Shiga, all of Japan

[73] Assignee: Kabushiki Kaisha Morita Seisakusho, Kyoto, Japan

[21] Appl. No.: 276,695

[22] Filed: Jun. 23, 1981

[30] Foreign Application Priority Data

Jun. 27, 1980 [JP] Japan ............................. 55-88060

[51] Int. Cl.³ .................................... G03B 41/16
[52] U.S. Cl. ........................... 378/40; 378/91
[58] Field of Search ....................... 378/39, 40, 91

[56] References Cited
U.S. PATENT DOCUMENTS 4,286,163  8/1981  Suzuki ........................... 378/40

Primary Examiner—Craig E. Church
Attorney, Agent, or Firm—Koda and Androlia

[57] ABSTRACT

This disclosure relates to the improvement of a tomograph for photographing the entire jaws which is designed to make an X-ray photograph of a curved plane section of an object by changing the rotating output of a motor for driving a rotary arm by using an eccentric cam means to control a film feed speed by the rotary output thus change. This apparatus includes a tachogenerator for converting the rotating output of the rotary arm driving motor into an electric output, a voltage shunting means for shunting the output of the tachogenerator to three paths, a reference point correction circuit and a changeover resistance means, and is capable of providing a clear X-ray photograph of a patient in the range of adults to children without necessity to change the eccentric cams nor the position of the patient.

1 Claim, 3 Drawing Figures (1)

(2)

(3)

TOMOGRAPH FOR PHOTOGRAPHING ENTIRE JAWS

BACKGROUND OF THE INVENTION

1. Field of the Invention

This invention relates to the improvements of a tomograph for photographing the entire jaws which is designed to obtain an X-ray photograph of the curved plane section of an object by transmitting the driving output of a driving motor for driving a rotary arm to a motor for feeding a film after having converted the output into an electric output by an eccentric cam means.

2. Prior Art

Concerning a method and an apparatus for obtaining an X-ray photograph of a curved plane section of the object by changing transfer factor of the rotating output of a rotary arm driving motor by an eccentric cam means (adapted to be rotated in accordance with rotation of the rotary arm) to control the film feed speed of a film feed device, the present applicant has already filed the following applications for above invention not only in Japan but also in the United States of America, Germany, Italy, and Finland respectively under U.S. Ser. No. 188,884, U.S. Ser. No. 131,689 and U.S. Ser. No. 131,709; German Patent Application No. P3010798.3, P3010799.4 and P3035436.0; Italian Patent Application No. 48220 A/80 and No. 48221 A/80; and Finnish Patent Application No. 802928.

The above-identified invention were designed to control a film feed speed by changing divided voltage output of potentiometer by an eccentric cam means which rotates in accordance with rotation of a rotary arm and leading the changed voltage to V/F converter circuit to thereby drive a pulse motor, and the curved plane section orbit of an object to be photographed was primarily specified by the configuration of the cam means. Accordingly, when the configuration of the object to be photographed, for example, the configuration of the dental arch was substantially the same, it was possible to continuously photograph a plurality of objects having no blurred points thereon, but when the objects are different in their configurations, it was impossible, in principle, to obtain a sharp picture of an object unless the object (patient) changed its position to be set or the cam used was replaced by one different in configuration.

SUMMARY OF THE INVENTION

Accordingly, a primary object of the invention is to provide a tomograph for photographing the entire jaws which is designed to readily obtain an X-ray photograph of a plane section of the entire jaws of all patients in the range of adults to children without changing an eccentric cam nor changing the position which a patient should take.

Another object of the invention is to provide a tomograph for photographing the entire jaws which has rendered it possible to improve the quality of X-ray photograph by correctly presetting a film feed speed.

The objects described above are achieved by a tomograph for photographing the entire jaws which is designed to photograph a curved plane section of an object P by irradiating X-rays from an X-ray generator while rotating a rotary arm by a rotary arm driving motor, the rotary arm having an X-ray generator and an X-ray film feed means Y in an opposed relation with each other as to the object P positioned between the generator and the film feed means, and simultaneously therewith, by converting the output of the rotary arm driving motor into an electric output and feeding the X-ray film by operating the film feed means Y, wherein the tompgraph comprises (1) an eccentric cam means predetermined in its configuration in accordance with the object P to be photographed, the cam means being mounted at a suitable place of the arm and adapted to be rotated in accordance with the rotation of the arm to thereby change the divided voltage output of a potentiometer; (2) a tachogenerator (G) directly connected to the rotary arm driving motor (IM) for rotating the rotary arm; (3) a voltage shunting means for shunting an electromotive force outputted from the tachogenerator (G) to three paths and deriving a reference point specified input voltage from the first path of the paths, deriving a signal input voltage variably set by the potentiometer from the second path of the paths, and deriving a reference point correction voltage capable of preset control from the third path of the paths; (4) a reference point correction circuit for subtracting the signal input voltage and reference point correction voltage; (5) a V/F converter circuit for inputting additional output obtained by adding output voltage of the reference point correction circuit to the reference point specified voltage into the converter circuit and generating a voltage pulse proportional to the additional output; (6) a changeover resistance means for selectively changing over voltage output to be supplied from the reference correction circuit to the V/F converter circuit; and (7) a pulse motor driving circuit for inputting a voltage pulse outputted from the V/F convereter circuit thereinto to thereby drive the film feed pulse motor for the film feed means.

The structure and characteristics of the invention will become more apparent from the detailed description of the invention taken in conjunction with the accompanying drawings showing, by way of example, only a preferred embodiment of the invention.

DETAILED DESCRIPTION OF THE INVENTION

A detailed description will now be given of a preferred embodiment of the invention with reference to the accompanying drawings.

Figure 1:
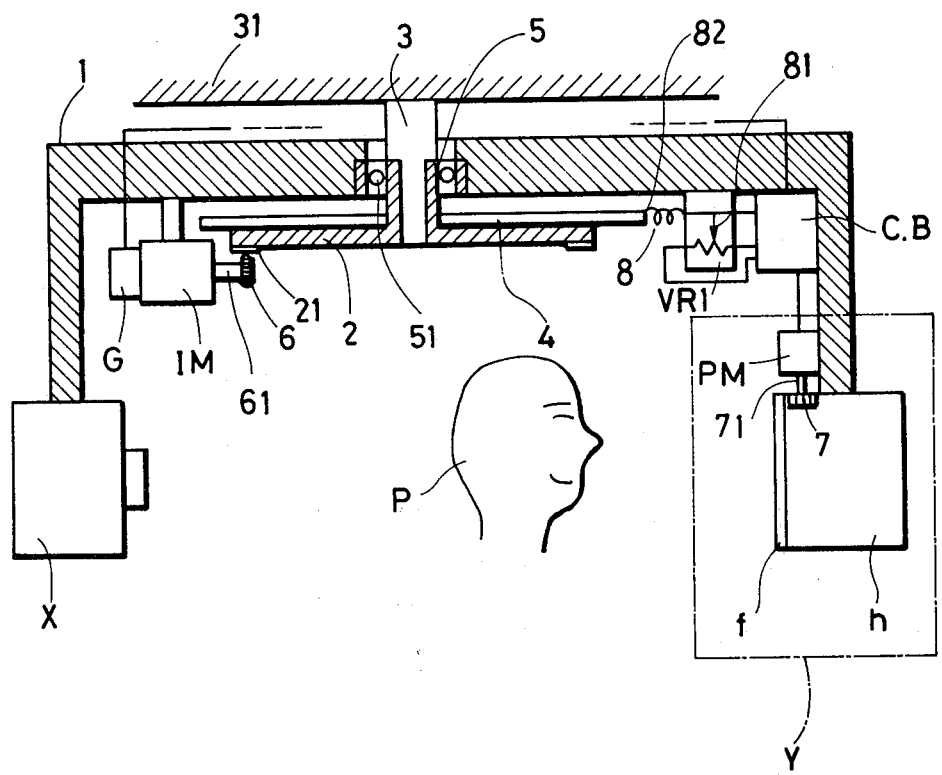
FIG. 1 shows a schematic structure of the invention.

FIG. 1 is a longitudinal sectional side view showing a mechanical structure of the invention. In the figure, the numeral 1 designates a rotary arm which rotates around a base shaft 3 suspended from a support base 31 and rotates circumferentially outwardly of an object (patient) P. The arm 1 is mounted at both ends thereof with an X-ray generator X and a film feed device Y in an opposed relation with each other. The numeral 2 designates a receiver plate fixed to the base shaft 3 having a rack 21 formed at the outer edge. The numeral 51 designates a ball bearing for smoothing the rotation of the arm 1 with respect to the base shaft 3. The character IM designates an induction motor used for a power supply and is fixed at a suitable plane of the rotary arm 1, and G designates a tachogenerator for converting rotating output into an electromotive force.

The induction motor IM is provied on the output shaft 61 thereof with a pinion gear 6 meshing with the rack 21 on the receiver plate 2, so that the rotating output of the induction motor IM drives the arm 1.

The output of the tachogenerator G is led into a control box CB through a lead-in wire. The eccentric cam means is constructed with an eccentric cam 4 mounted on the receiver plate 2 and provided with the configuration thereof predetermined in accordance with the configuration of an object P to be photographed, a spring 8 and an abutment plate 82, and changes the transfer factor of the rotating output of the tachogenerator G in accordance with the number of rotation of the motor for driving the rotary arm 1 by specifying signal input voltage by moving a slider 81 of potentiometer VR1 in accordance with rotation of the rotary arm 1.

The numeral 7 designates a pinion gear fixed to an output shaft 71 of a pulse motor PM, and the gear 7 functions to feed a film by moving a film cassette f in accordance with the rotation of the pulse motor PM. This photographing apparatus irradiates X-rays on an object P by an X-ray generator X while rotating the rotary arm 1 around the object P and at the same time makes a tomogram of the curved plane of the object P by controlling the feed of film cassette f by the film feed device Y. The orbital plane of a predetermined plane section to be photographed is relatively determined both by a film feed speed and by rotating speed of the rotary arm. Accordingly, when the rotating speed of the arm is constant, it is possible to change the orbital plane of a plane section to be photographed by changing the film feed speed. The apparatus of the invention makes it possible to make an X-ray photographic picture of the curved plane section of the entire jaws of an object in the range of adults to children by merely changing a resistor by a changeover resistance means without replacing an eccentric cam but with the photographing position of the object P kept fixed in position. The principle of the apparatus of the invention will become more apparent from the description thereof that follows.

Figure 2:
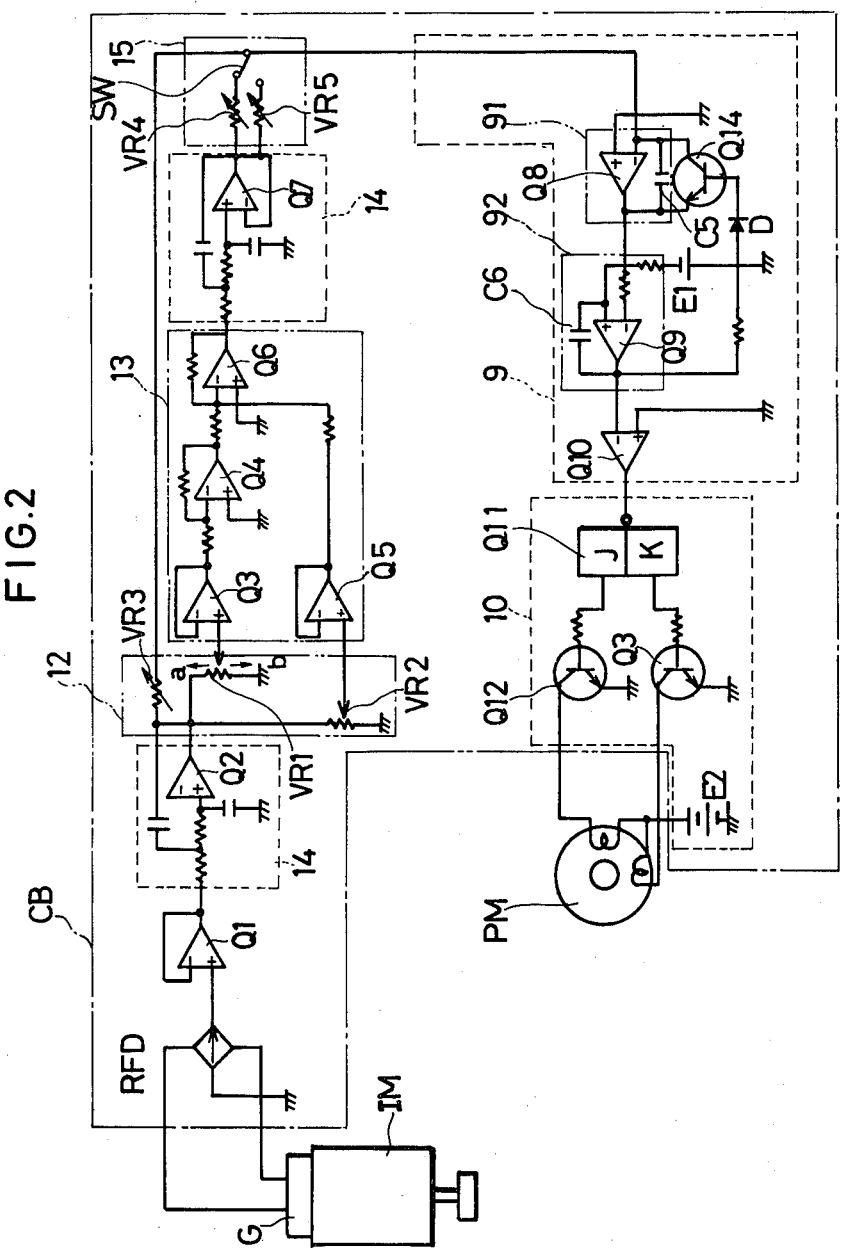
FIG. 2 shows a schematic block diagram of the invention.

FIG. 2 is a schematic structure of a control circuit mounted inside of the control box CB. In the figure, the character IM designates an induction motor for driving the rotary arm; and G designates a tachogenerator for determining driving power of a pulse motor PM for feeding a film in a film feed device Y by converting the rotational frequency of the induction motor IM into an electromotive force.

The character FRD designates a bridge rectifier for rectifying AC output of the tachogenerator G; Q1 a buffer amplifier; and 14 designates a low-pass filter for removing high-frequency noise component.

The numeral 12 designates a voltage shunting means for shunting the electromotive force of the tachogenerator from which force high-frequency component has been removed through the low-pass filter, the voltage shunting means including three potentiometers VR1, VR2 and VR3. A slider 81 of the potentiometer VR1 is moved by the eccentric cam means in accordance with the rotation of the rotary arm 1 and the dividing output of the potentiometer VR1 is inputted into a reference point correction circuit 13 in the form of a signal input voltage. On the other hand, the potentiometer VR2 is designed to make a preset control of the divided output thereof by a dial (not shown) and to input the output into the subtraction input circuit in the form of a reference point correction voltage. The third potentiometer VR3 is also designed to make a preset control of the divided output and to set an orbital plane for photographing an object and, after having set the lowest speed of a film feed speed at photographing point which is necessary for photographing a curved plane section of the object P, to fix and to use the thus set lowest speed value as a reference point specified input voltage.

The numeral 13 designates a reference point correction circuit for subtracting the reference point correction voltage from a signal input voltage. The circuit 13 comprises voltage follower amplifiers Q3 and Q5 for inputting signal input voltage and reference point correction voltage thereinto, an inverter 24 for controlling the gain thereof to 1 and inverting and outputting the signal input voltage, and an inversion adder Q6.

A V/F converter circuit 9 includes an integration circuit 91, a comparison circuit 92 which inverts the output of the circuit 92 when the output of the integration is brought into agreement with reference voltage E1 of the comparison circuit 92 by comparison of the reference voltage E1 with the output of the integration circuit 91, a transistor Q14 which is driven by the inverted output of the comparison circuit 92 and returns the output of the integration circuit 91 to a zero level, and a buffer amplifier Q10 which further inverts the inverted output of the comparison circuit 92 and triggers the flip-flop Q11 of the film feed motor PM. The V/F converter circuit 9 inputs thereinto an additional output obtained by adding the output voltage of the reference point correction circuit 13 to a reference input voltage specified by the potentiometer VR1, and specified the number of pulses outputted by changably setting the time constant of the integration circuit 91 of the changeover resistance selected by a changeover resistance means 15. Namely, the time constant of the integration circuit 91 is also increased or decreased in response to the relative resistance value of the changeover resistance, with the result that the output pulse of the V/F converter unit is, in turn, changed to thereby change and control the number of rotations of the pulse motor PM.

The numeral 10 disignates a drive circuit for a film feed motor PM, and the drive circuit 10 includes a flip-flop Q11 which is triggered by receiving the output pulse of the V/F converter circuit 9, and drives the transistors Q12 and Q13 which are alternately driven by the output of the flip-flop Q11 and also drive the film feed motor PM. The reference character E2 designates a driving power source for the film feed motor PM which is rotated by pulse.

The numeral 15 designates a changeover resistance means. The means 15 in the embodiment illustrated is designed to make changeover connection of the two changeover resistors VR4 and VR5 which are different in resistance value and to set the time constant of the integration circuit 91 of the V/F converter circuit 9.

A description will now be given of the photographing principle of the apparatus of the invention. First, the time constant of the integration circuit 91 is set by selecting a changeover resistor to be connected to the integration circuit 91 of the V/F converter circuit 9 by a changeover resistance means 15 in response to the configuration of the object P. Next, after the potentiometer VR1 has been controlled by changing a position of the arm so that a signal output voltage that specifies a minimum speed may be outputted in photographing by the control of the potentiometer VR1, the potentiometer VR2 is controlled so as to countervail the signal input voltage with reference point correction voltage, and preset control of the reference point correction circuit 13 is made so as to reduce the output of the circuit 13 to zero when the signal output voltage is in the stae of the signal input voltage specifying a minimum speed. Accordingly, the minimum speed of the film feed speed holds a constant value specified by the potentiometer VR3 even if any changeover resistance is selected by the preset control but the speed other than the minimum speed is specified by the value of the changeover resistor. As a result, successive changeover of the changeover resistance means 15 by using the apparatus of the invention in obtaining an X-ray photograph of a curved plane section of the dental arch makes it possible to set a minimum value of the film feed speed, namely, a photographing orbit common to the front tooth region and which is shown in FIG. 3(1).

Figure 3:
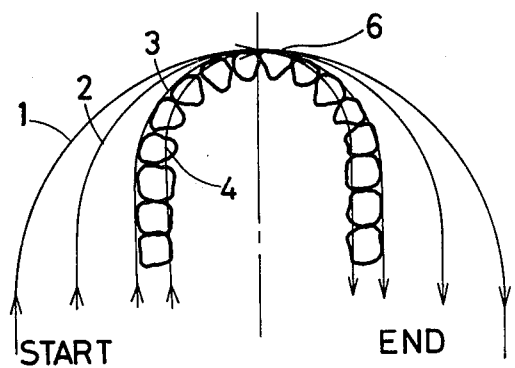
FIGS. 3(1) through 3(3) shows an explanatory diagram for illustrating the photographing principle of the invention when a tomogram is made of the curved plane of the dental arch.
Figure 3:
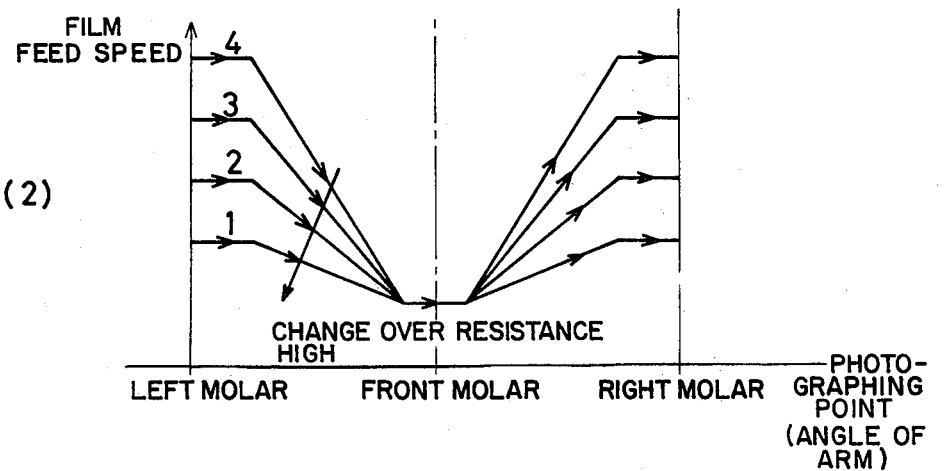
Figure 3:
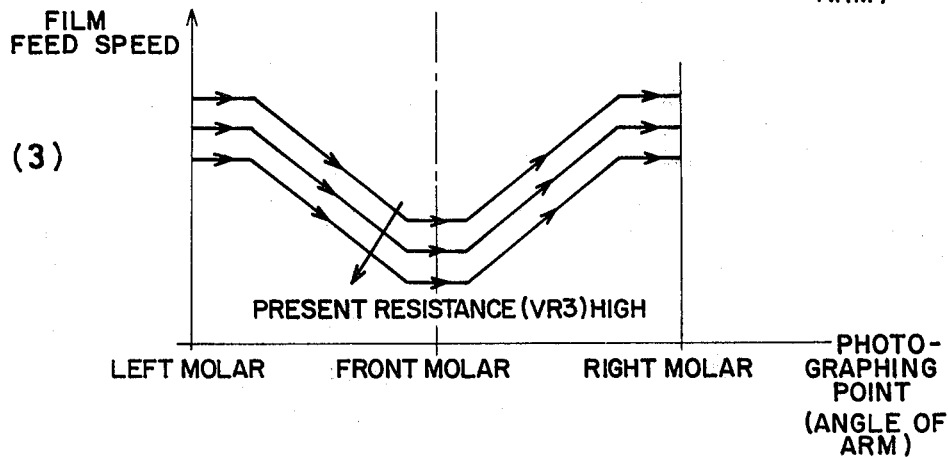

It should readily be understood that the changeover resistor selected in response to the orbital plane in this case is in the relation shown in FIG. 3(2), and accordingly as the value of the changeover resistor is decreased, the film feed speed is also increased from the principle tomography for photographing a curved plane, but the orbital plane to be photographed is conversely reduced.

FIG. 3(3) is a diagram illustrating a relation between the film feed speed and the photographing region in the case where a changeover resistor is set at zero, namely, where the value of the preset resistor VR3 alone is changed.

A description has been given as above of the structure and photographing principle of the invention, and the invention provides the following advantages:

1. Since the invention makes it possible to correctly control the maximum value and minimum value of the film feed speed, improvement can be made in the quality of X-ray photograph in tomographic photographing. 2. Since the invention makes it possible to make a tomogram of the large and small dental arches over the front tooth region merely by variously selecting the resistance value connected to the V/F converter circuit 9 by changeover contact SW, the invention can relieve an operator of the trouble to replace an eccentric cam or to displace the photographing position of an object P as opposed to the conventional devices and renders it easy to photograph any object in the range of adults to children.

It should be understood that the invention can find application not only in the tomograph for photographing the entire jaws in dental treatment, but also in other fields of tomographic use.

I claim:
1. A tomograph for photographing the entire jaws which is designed to photograph a curved plane section of an object which includes a rotary arm rotated by a rotary arm driving motor, said rotary arm having provided thereon an X-ray generator and an X-ray film feed means in an opposed relation with each other with the object positioned between the X-ray generator and the film feed means, said tomograph being characterized in that it comprises:
   an eccentric cam means predetermined in its configuration in accordance with said object to be photographed, said cam means being mounted at a suitable place of said rotary arm and adapted to be rotated in accordance with the rotation of said arm;
   a potentiometer cooperating with said eccentric cam, said potentiometer changing resistance in response to the rotation of said rotating arm;
   a tachogenerator directly connected to said rotary arm driving motor for generating an electromotive force;
   a voltage shunting means for dividing said electromotive force outputted from said tachogenerator into three paths and for deriving a reference point input voltage from a first path of said paths, for deriving a signal input voltage by applying a second path of said paths to the potentiometer and for deriving a presettable reference point correction voltage from a third path of said paths;
   a reference point correction circuit for subtracting said signal input voltage and reference point corection voltage;
   a V/F converter circuit receiving an additional output obtained by adding an output of said reference point correction circuit to said reference point input voltage and for generating a voltage pulse proportional to said additional output;
   a changeover resistance means for selectively changing said output of said reference correction circuit supplied to said V/F converter circuit;
   a pulse motor for driving said film feed means; and
   a pulse motor driving circuit receiving said voltage pulse outputted from said V/F converter circuit thereinto to thereby drive the film feed pulse motor for said film feed means.

* * * * *